US006805704B1

(12) United States Patent
Hoyns

(10) Patent No.: US 6,805,704 B1
(45) Date of Patent: Oct. 19, 2004

(54) INTRALUMINAL STENTS

(75) Inventor: Dirk V. Hoyns, Conyers, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 96 days.

(21) Appl. No.: 09/603,409

(22) Filed: Jun. 26, 2000

(51) Int. Cl.[7] .................................................. A61F 2/06
(52) U.S. Cl. ...................................................... 623/1.15
(58) Field of Search ................................ 623/1.15, 1.1, 623/1.13, 1.14, 1.16, 1.17, 1.18–1.22

(56) References Cited

U.S. PATENT DOCUMENTS

| | | | |
|---|---|---|---|
| 4,886,062 A | 12/1989 | Wiktor | |
| 5,019,090 A | 5/1991 | Pinchuk | |
| 5,122,154 A | 6/1992 | Rhodes | |
| 5,133,732 A | 7/1992 | Wiktor | |
| 5,314,472 A | 5/1994 | Fontaine | |
| 5,342,348 A | 8/1994 | Kaplan | |
| 5,443,478 A | 8/1995 | Purdy | |
| 5,449,373 A | 9/1995 | Pinchasik et al. | |
| 5,507,767 A | 4/1996 | Maeda et al. | |
| 5,514,154 A | 5/1996 | Lau et al. | |
| 5,549,662 A | 8/1996 | Fordenbacher | |
| 5,562,697 A | 10/1996 | Christiansen | |
| 5,569,295 A | 10/1996 | Lam | |
| 5,575,816 A | 11/1996 | Rudnick et al. | |
| 5,591,197 A | 1/1997 | Orth et al. | |
| 5,591,198 A | 1/1997 | Boyle et al. | |
| 5,593,417 A | 1/1997 | Rhodes | |
| 5,603,721 A | 2/1997 | Lau et al. | |
| 5,607,445 A | 3/1997 | Summers | |
| 5,630,829 A | 5/1997 | Lauterjung | |
| 5,649,952 A | 7/1997 | Lam | |
| 5,653,727 A | 8/1997 | Wiktor | |
| 5,665,115 A | 9/1997 | Cragg | |
| 5,670,161 A | 9/1997 | Healy et al. | |
| 5,695,516 A | 12/1997 | Fischell et al. | |
| 5,697,971 A | 12/1997 | Fischell et al. | |
| 5,716,396 A | 2/1998 | Williams, Jr. | |
| 5,725,547 A | 3/1998 | Chuter | |
| 5,728,150 A | 3/1998 | McDonald et al. | |
| 5,735,893 A | 4/1998 | Lau et al. | |
| 5,741,327 A | 4/1998 | Frantzen | |
| 5,755,776 A | 5/1998 | Al-Saadon | |

(List continued on next page.)

FOREIGN PATENT DOCUMENTS

| | | |
|---|---|---|
| EP | 0 790 041 A2 | 8/1997 |
| EP | 0 895 759 A1 | 2/1999 |
| EP | 0 958 794 A2 | 11/1999 |

*Primary Examiner*—(Jackie) Tan-Uyen T. Ho
(74) *Attorney, Agent, or Firm*—Kirkpatrick & Lockhart LLP

(57) ABSTRACT

An intraluminal stent placeable in the lumen of the human body. Includes a generally tubular wall having a filigree-like pattern of interconnected links and open work. The pattern includes nodes that have a central hub and three arms connected to the hub. The arms are arranged circumferentially about the hub and lie adjacent the next adjacent arm of the node in a spiral-like fashion. The arms are connected to other components of the stent which, themselves, may comprise other nodes. The nodes are arranged in repeatable clusters. The disclosure also relates to a technique for making a stent and for mounting a stent on a delivery catheter by which the stent may be crimped onto the catheter in its lowest profile configuration.

37 Claims, 13 Drawing Sheets

U.S. PATENT DOCUMENTS

| | | |
|---|---|---|
| 5,759,192 A | 6/1998 | Saunders |
| 5,766,237 A | 6/1998 | Cragg |
| 5,766,238 A | 6/1998 | Lau et al. |
| 5,776,161 A | 7/1998 | Globerman |
| 5,800,456 A | 9/1998 | Maeda et al. |
| 5,810,872 A | 9/1998 | Kanesaka et al. |
| 5,814,063 A | 9/1998 | Freitag |
| 5,817,126 A | 10/1998 | Imran |
| 5,824,036 A | 10/1998 | Lauterjung |
| 5,824,045 A | 10/1998 | Alt |
| 5,824,053 A | 10/1998 | Khosravi et al. |
| 5,833,699 A | 11/1998 | Chuter |
| 5,836,964 A | 11/1998 | Richter et al. |
| 5,836,966 A | 11/1998 | St. Germain |
| 5,843,168 A | 12/1998 | Dang |
| 5,855,597 A | 1/1999 | Jayaraman |
| 5,861,027 A | 1/1999 | Trapp |
| 5,868,781 A | 2/1999 | Killion |
| 5,868,782 A | 2/1999 | Frantzen |
| 5,876,432 A | 3/1999 | Lau et al. |
| 5,879,370 A | 3/1999 | Fischell et al. |
| 5,879,381 A | 3/1999 | Moriuchi et al. |
| 5,895,406 A | 4/1999 | Gray et al. |
| 5,902,317 A | 5/1999 | Kleshinski et al. |
| 5,906,639 A | 5/1999 | Rudnick et al. |
| 5,907,893 A | 6/1999 | Zadno-Azizi et al. |
| 5,911,732 A | 6/1999 | Hojeibane |
| 5,911,754 A | 6/1999 | Kanesaka et al. |
| 5,913,895 A | 6/1999 | Burpee et al. |
| 5,913,896 A | 6/1999 | Boyle et al. |
| 5,913,897 A | 6/1999 | Corso, Jr. et al. |
| 5,922,005 A | 7/1999 | Richter et al. |
| 5,922,020 A | 7/1999 | Klein et al. |
| 5,922,021 A | 7/1999 | Jang |
| 5,925,061 A | 7/1999 | Ogi et al. |
| 5,931,866 A | 8/1999 | Frantzen |
| 5,935,162 A | 8/1999 | Dang |
| 5,938,682 A | 8/1999 | Hojeibane et al. |
| 5,948,016 A | 9/1999 | Jang |
| 5,968,088 A | 10/1999 | Hansen et al. |
| 5,972,028 A | 10/1999 | Rabenau et al. |
| 5,980,552 A | 11/1999 | Pinchasik et al. |
| 5,980,553 A | 11/1999 | Gray et al. |
| 5,994,667 A | 11/1999 | Merdan et al. |
| 6,010,529 A | 1/2000 | Herweck et al. |
| 6,022,370 A | 2/2000 | Tower |
| 6,027,526 A | 2/2000 | Limon et al. |
| 6,027,527 A | 2/2000 | Asano et al. |
| 6,032,674 A | 3/2000 | Eggers et al. |
| 6,033,433 A | 3/2000 | Ehr et al. |
| 6,039,756 A | 3/2000 | Jang |
| 6,042,597 A | 3/2000 | Kveen et al. |
| 6,053,940 A | 4/2000 | Wijay |
| 6,059,808 A | 5/2000 | Boussignac et al. |
| 6,063,113 A | 5/2000 | Kavteladze et al. |
| 6,066,167 A | 5/2000 | Lau et al. |
| 6,071,307 A | 6/2000 | Rhee et al. |
| 6,086,604 A | 7/2000 | Fischell et al. |
| 6,090,127 A | 7/2000 | Globerman |
| 6,096,072 A | 8/2000 | Kanesaka et al. |
| 6,107,004 A | 8/2000 | Donadio, III |
| 6,117,165 A | 9/2000 | Becker |
| 6,123,721 A | 9/2000 | Jang |
| 6,136,023 A | 10/2000 | Boyle |
| 6,162,243 A | 12/2000 | Gray et al. |
| 6,171,334 B1 | 1/2001 | Cox |
| 6,174,328 B1 | 1/2001 | Cragg |
| 6,190,406 B1 | 2/2001 | Duerig et al. |
| 6,193,744 B1 | 2/2001 | Ehr et al. |
| 6,203,569 B1 | 3/2001 | Wijay |
| 6,217,608 B1 | 4/2001 | Penn et al. |
| 6,221,100 B1 | 4/2001 | Strecker |
| 6,231,599 B1 * | 5/2001 | Ley .................... 623/1.15 |
| 6,235,053 B1 | 5/2001 | Jang |
| 6,238,409 B1 | 5/2001 | Hojeibane |
| 6,238,430 B1 | 5/2001 | Klumb |
| 6,241,757 B1 | 6/2001 | An et al. |
| 6,241,760 B1 | 6/2001 | Jang |
| 6,245,101 B1 | 6/2001 | Drasler et al. |
| 6,334,870 B1 * | 1/2002 | Ehr et al. ............. 623/1.1 |
| 6,395,020 B1 * | 5/2002 | Ley et al. ............. 623/1.15 |

* cited by examiner

INTRALUMINAL STENTS

FIELD OF THE INVENTION

This invention relates to stents placeable in a lumen of the human body to maintain patency of the lumen.

BACKGROUND OF THE INVENTION

The use of stents has become common in connection with procedures where it is desired to reinforce the wall of a vessel in the human body to maintain the patency of the lumen and reduce the risk of constriction of the lumen or collapse of the vessel wall. Stents have come into common use in connection with angioplasty procedures in which a blood vessel in the human body, having become obstructed, is dilated to restore the flow area of the lumen. A stent placed in the treated region of the lumen serves as a scaffold to support the vessel wall that defines the lumen. Stents may be placed as part of a surgical procedure or, as is more often the case, percutaneously, by navigating a slender catheter, on which the stent is mounted into and through the patient's vasculature to the target site. Stents also are used in connection with other body lumens, such as in the urinary and biliary tracts, among others.

Most stents are generally tubular in shape and may be classified either as self-expanding or as balloon expandable. Self-expanding stents characteristically are in their expanded configuration when in a free, released state. In order to advance a self-expanding stent to the deployment site in the vessel, the stent is contracted to its small diameter (low profile) dimension and is mounted to the distal end of a delivery catheter that maintains the stent in its low profile configuration as the catheter is advanced to the target site. The stent is deployed by freeing the stent from the catheter to enable the stent to self-expand, under its inherent resilience, into supportive engagement with the vessel wall. The delivery catheter then can be removed from the patient, leaving the stent in place. In contrast, a balloon expandable stent does not rely on inherent resilience for its use or operation. Rather, a balloon expandable stent typically is formed as a metal tubular structure defined by a selected pattern of interconnected structures and links configured to enable the diameter of the stent to be expanded forcibly, as by a balloon, from its low profile diameter to a larger diameter at which it can support the vessel wall. During such expansion, the metallic stent undergoes plastic deformation and retains its expanded diameter. The balloon deployment catheter then can be deflated and withdrawn, leaving the stent in place. Another class of stents includes those formed from a shape memory alloy, such as a nickel-titanium alloy (nitinol). The alloy has a thermal-dependent memory in that it will maintain a stable configuration, as in a low profile configuration suitable for delivery by a catheter, but will return to its memory shape (e.g. to expand to a larger, vessel-supporting diameter) in response to a thermal event such as injecting warm saline into the vessel to trigger the shape memory phenomenon or exposing-the stent to body temperature. Such alloys also can be made to exhibit superelastic properties Among the desirable features of a stent are that it should have sufficient hoop strength to support the vessel against the stresses that the vessel can be expected to impose on the deployed stent. The degree of scaffolding, a measure of the percentage of cylindrical area defined by the expanded stent as compared to the void spaces between its metal structures and links, should be selected to provide the desired balance between structural strength of the stent and exposure of the inner surface of the vessel to the lumen. It is important that the stent be capable of being contracted to a low profile diameter that is sufficiently small to facilitate percutaneous insertion of the stent and navigation of the stent through the sometime tortuous vasculature. The longitudinal flexibility of the stent also is an important characteristic, particularly in settings in which the stent must be navigated through tortuous vessels in order to reach the intended deployment site. Longitudinal flexibility also is important after the stent has been expanded in order that the natural curvature of the body lumen, which typically is deformed when the balloon is inflated, can return to its natural shape after the stent has been deployed and the delivery catheter removed. Also among the desirable characteristics of a stent is that it should have a sufficiently large expansion ratio, that is, the ability to expand from its low profile configuration to as large a diameter as can reasonably be expected, in order to treat the condition at hand. A large expansion ratio enables the physician to perform a procedure with an additional measure of confidence that if the original assessment of proper stent size is smaller than what is actually required, the stent can be expanded to a still larger diameter. Further, in many cases, it is important that the stent, when expanded radially, does not contract substantially, if at all, in length as it is deployed. Also among the desirable characteristics of a stent, particularly with balloon expandable stents, is that the expansion of the stent components be relatively uniformly distributed. Additionally, it is desirable that when the stent is expanded from its low profile to its deployed diameter, it does not have stress points that, upon expansion or after deployment, could lead to fracture of portions of the stent.

It is among the general objects of the invention to provide an improved stent construction and mode of operation by which the foregoing desirable characteristics of a stent may be obtained.

SUMMARY OF THE INVENTION

The invention is embodied in a tubular stent in which the wall of the stent is defined by a filigree-like pattern defined by regions of interconnected metal members and openwork. The pattern is characterized by a plurality of nodes arranged in clusters, each cluster comprising a group of nodes. Each of the nodes includes a central hub and at least three arms connected to and circumscribing, partially, the hub. When the stent is in its low profile, unexpanded state, each arm is arranged circumferentially about the hub of the node and lies closely adjacent to the next adjacent arm of the node in a spiral-like fashion. Each of the arms in a node is connected at a transition region to an adjacent node by being connected to the outer end of an arm of that adjacent node, the connected arms and transition region together defining a link between adjacent nodes. When the stent is expanded, as by a balloon catheter, the links uncoil. The links uncoil differentially, the degree to which a particular link uncoils depending on the degree to which the link is oriented in a generally circumferential direction. A link that is oriented in a generally circumferential direction may uncoil more than a link that extends in a direction that is closer to the axial direction of the stent. The nodes enable each of the links to unfold to the extent necessary to respond to the radial and axial forces applied to the stent during balloon expansion. The nodes are free to shift and reorient themselves in response to the applied forces of expansion.

One embodiment of the invention (FIG. 3) includes clusters that define a pattern of nodes arranged generally hexagonally. In another embodiment (FIG. 13), the nodes may be packed more closely together and are disposed to lie generally helically along the stent with each node along the helix being serially connected by a link to the next adjacent nodes on that helix.

In another aspect of the invention, the stent is formed by laser cutting the pattern of the stent from a metal tube having a diameter selected to correspond to the lowest profile that the stent is expected to have, typically the diameter that the stent will have when mounted and crimped onto the balloon of a delivery catheter. In order to load the stent onto the deflated balloon, the stent is preliminarily expanded slightly, for example, by advancing a tapered mandrel through the stent to increase its diameter sufficiently so that it can be slid onto the balloon. Once in position on the balloon, the stent then is crimped firmly about the balloon, with the stent returning toward its lowest profile configuration during the crimping process.

It is among the objects of the invention to provide an intraluminal stent that can be delivered while being maintained in a very low profile, yet in which the stent has a high degree of longitudinal flexibility to facilitate navigation through tortuous vessels; to provide an intraluminal stent that has sufficient flexibility in its expanded, deployed state to enable the vessel to return toward its natural shape; to provide such a'stent with a desirably high degree of longitudinal flexibility that has a large expansion ratio between its low profile and expandable diameters; to provide a stent that does not shorten adversely when it is deployed; and to provide a stent that, when it expands, maintains a relatively uniform distribution of its components and to provide such a stent with sufficient radial strength to provide luminal patency.

BRIEF DESCRIPTION OF THE DRAWINGS

The foregoing and other objects and advantages of the invention will be appreciated more fully from the following further description thereof, with reference to the accompanying drawings in which.

DESCRIPTION OF THE ILLUSTRATED EMBODIMENTS

Figure 1:
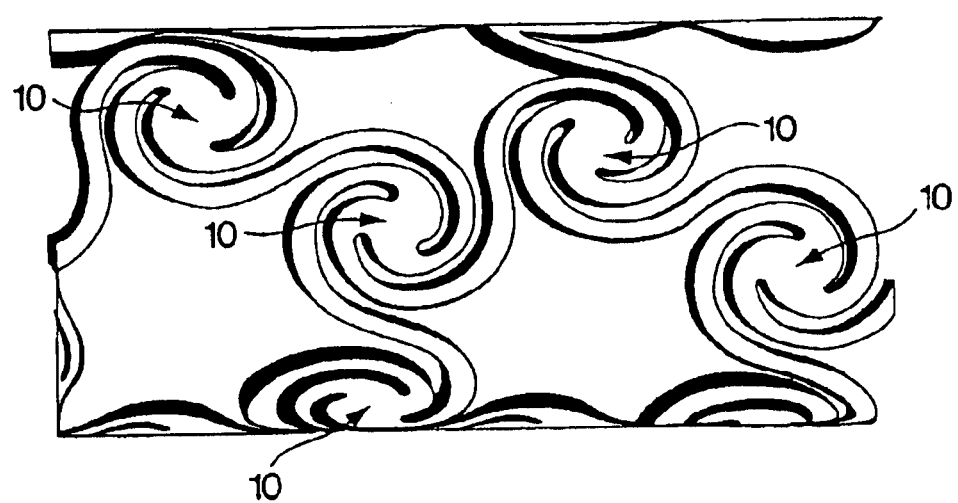
FIG. 1 is an illustration of a tubular stent incorporating one embodiment of the invention in which the nodes are arranged in hexagonal clusters, with the stent being in its low profile configuration.
Figure 2:
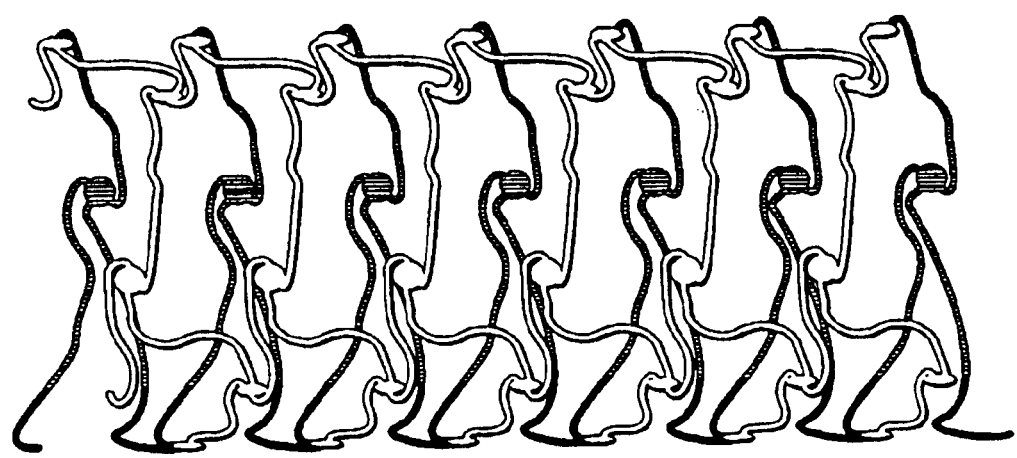
FIG. 2 is an illustration of the stent in FIG. 1 after expansion, as by a balloon catheter.

FIG. 1 illustrates one embodiment of a stent embodying the principles of the invention. The stent may be formed from a tube of stainless steel (316L) or titanium although other metals suitable for use in a stent may be employed, including shape memory alloys, as will be appreciated by those skilled in the art. The stent may be manufactured by any of a number of techniques known and in use in the prior art (such as etching and laser ablation), although the preferred approach is to manufacture it using laser ablation in which a solid-walled tube is rotated and translated about its longitudinal axis while a laser beam selectively ablates regions of the tube to form a filigree-like pattern. For example, the stent may be made using a neodimium-YAG laser. The width of the laser beam may be controlled to be quite small, of the order of about 0.002 inches. Such laser etching techniques in the manufacture of stents are known to those skilled in the art as disclosed in, for example, U.S. Pat. Nos. 4,762,128; 5,345,057; 5,356,423; 5,788,558; 5,800,526 and 5,843,117. The present invention relates to a pattern for such a stent that is characterized by a plurality of nodes where the nodes have a central hub and three arms projecting from the hub, with the arms being wrapped partly about the hub in somewhat of a spiral configuration. The nodes are arranged in clusters that can have varying geometric patterns, one of which is shown in FIGS. 1–6.

Figure 3:
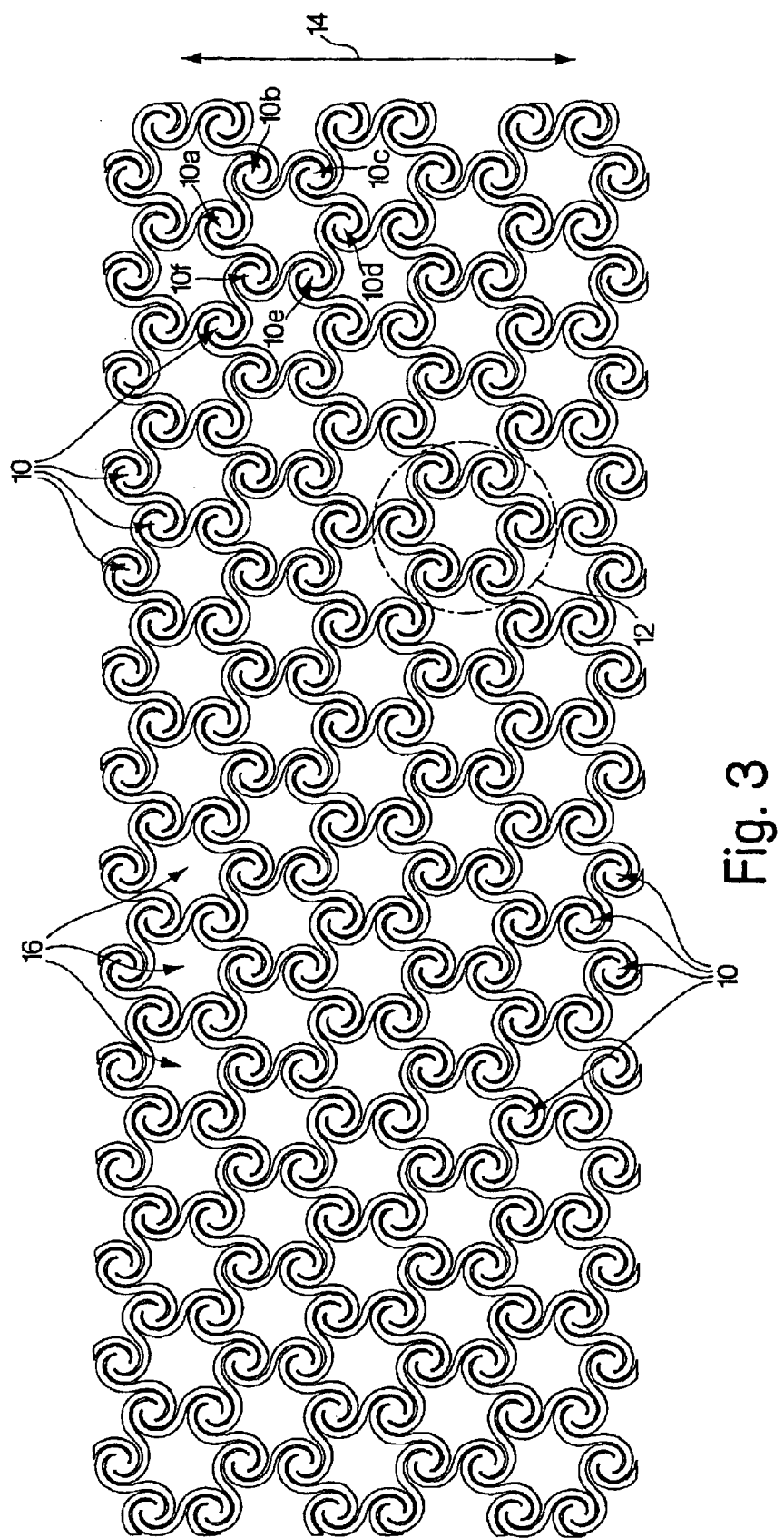
FIG. 3 is an illustration of the pattern of the stent of FIG. 1 shown before expansion and lying in a flat plane.
Figure 6:
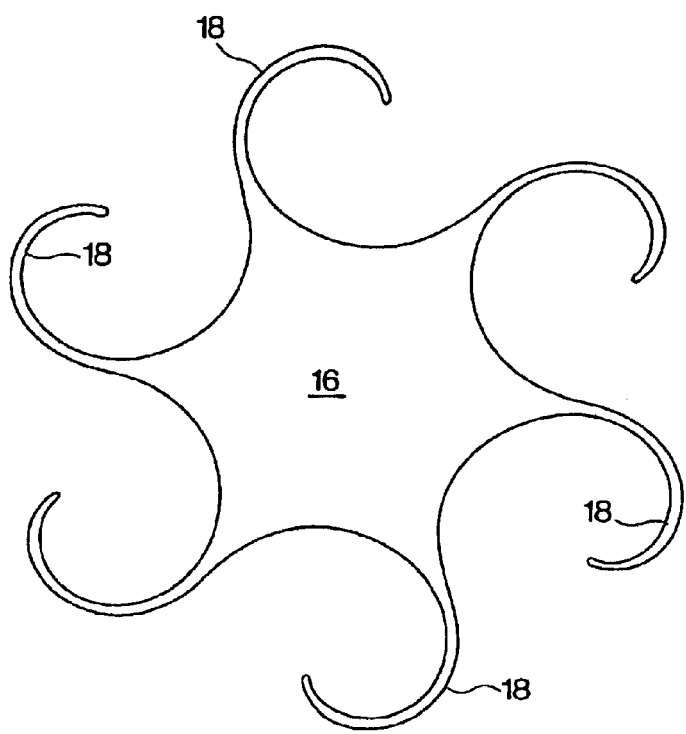
FIG. 6 is a diagram of the repeating cell pattern defined by a single hexagonal cluster of nodes.

FIG. 3 illustrates the invention in which the cylindrical wall of the stent is shown, for ease of explanation, as it would appear if the cylinder was slit longitudinally and laid out in a flat plane. In this embodiment, the arrangement can be seen to include a plurality of nodes 10 arranged to define a plurality of hexagonally-shaped clusters, one of which is encircled in phantom at 12. Each cluster 12 in this embodiment may be considered as having nodes 10a, 10b, 10c, 10d 10e and 10f that are oriented with the first node 10a (in the 12 o'clock position) and the fourth node 10d (in the 6 o'clock position) being aligned in a circumferential direction indicated by arrow 14. The nodes 10a–10f in an individual cluster may be equiangularly spaced about the center of the cluster. Except for the nodes 10 at the ends of the stent, the second and third nodes 10b, 10c serve as the fifth and sixth nodes 10e, 10f of the next adjacent hexagonal cluster. It also may be noted that each node may be considered to be in any one of three positions (10A–10F) because each node may be considered as being shared by three clusters that incorporate and surround that node. Thus, for example, in FIG. 4 one node may be designated as 10C, E, A, an adjacent node may be designated as 10B, D, F. It will be appreciated that each pair of adjacent clusters shares a pair of three-arm nodes. The open region defined within each cluster 12 may be considered as defining an open cell 16. In the hexagonal configuration illustrated in FIGS. 1 and 3, each cell 16 is characterized by an open central portion and six open curled fingers 18 radiating outwardly from the central portion of the cell as shown in FIG. 6. In a laser-cut device, the minimum width of the open curled fingers 18 may be determined by the width of the laser cutting beam which may be of the order of 0.002 inch wide.

Figure 4:
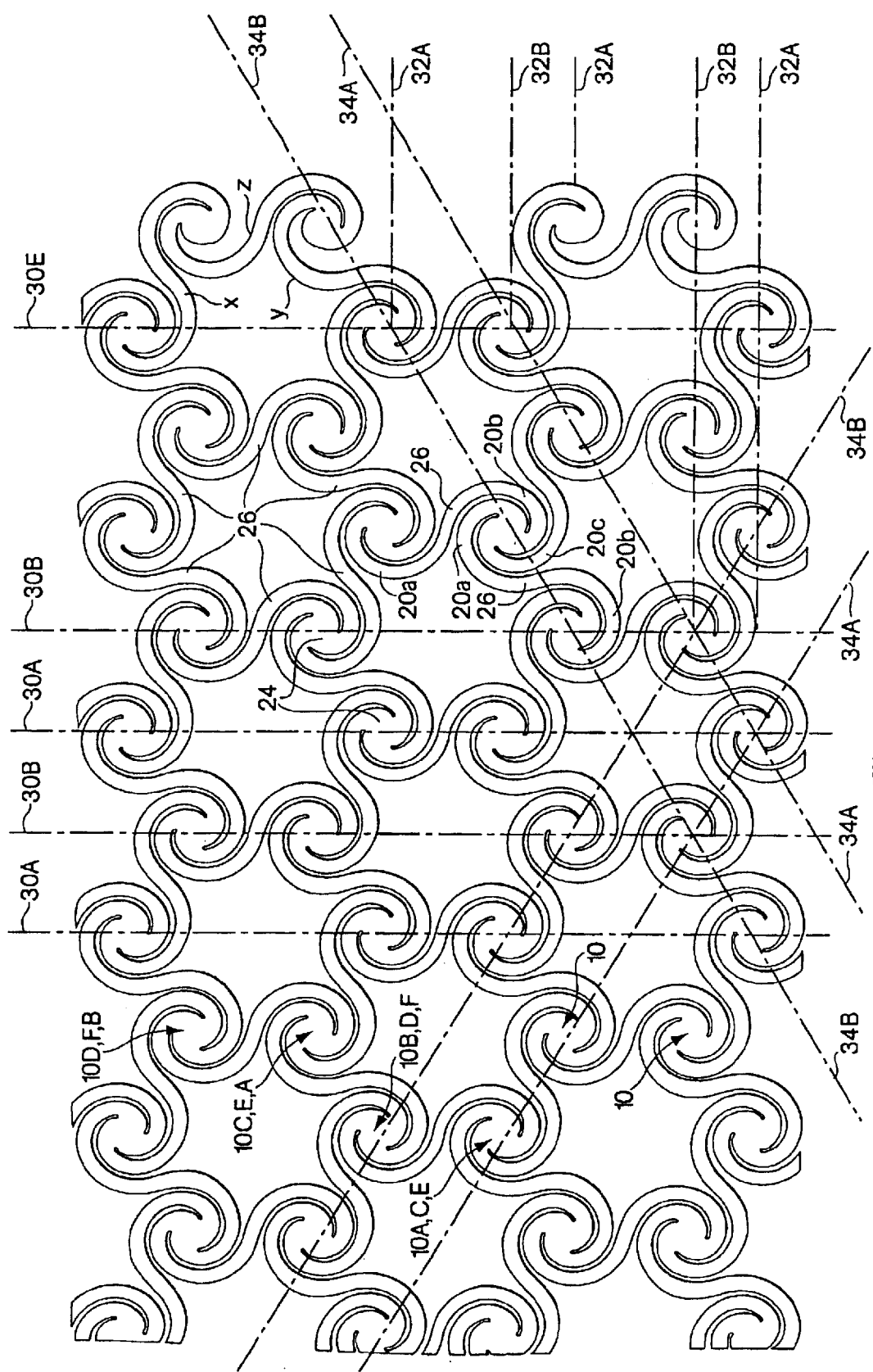
FIG. 4 is an enlarged illustration of a group of clusters of the stent pattern illustrated in FIG. 3.
Figure 5:
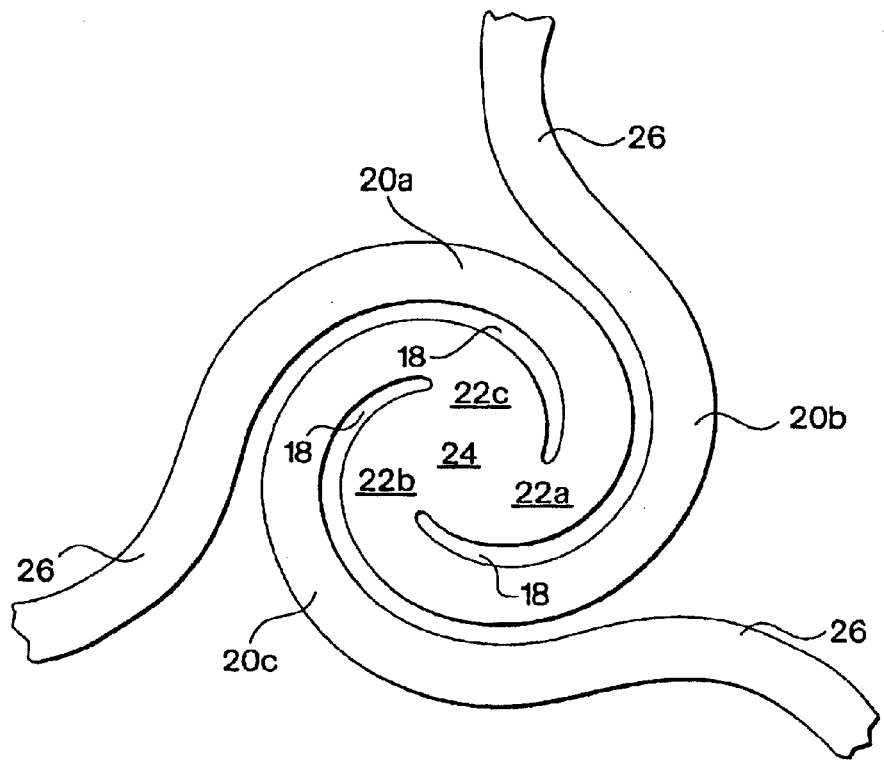
FIG. 5 is a greatly enlarged illustration of a single node.
Figure 7:
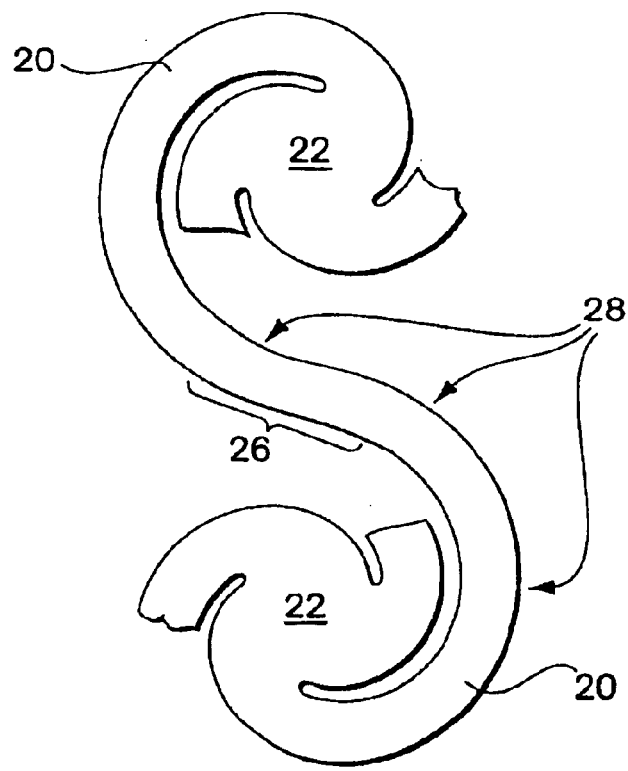
FIG. 7 is a fragmented illustration of a pair of adjacent nodes aligned circumferentially and showing the configuration of an individual circumferentially oriented link connecting the nodes.
Figure 14:
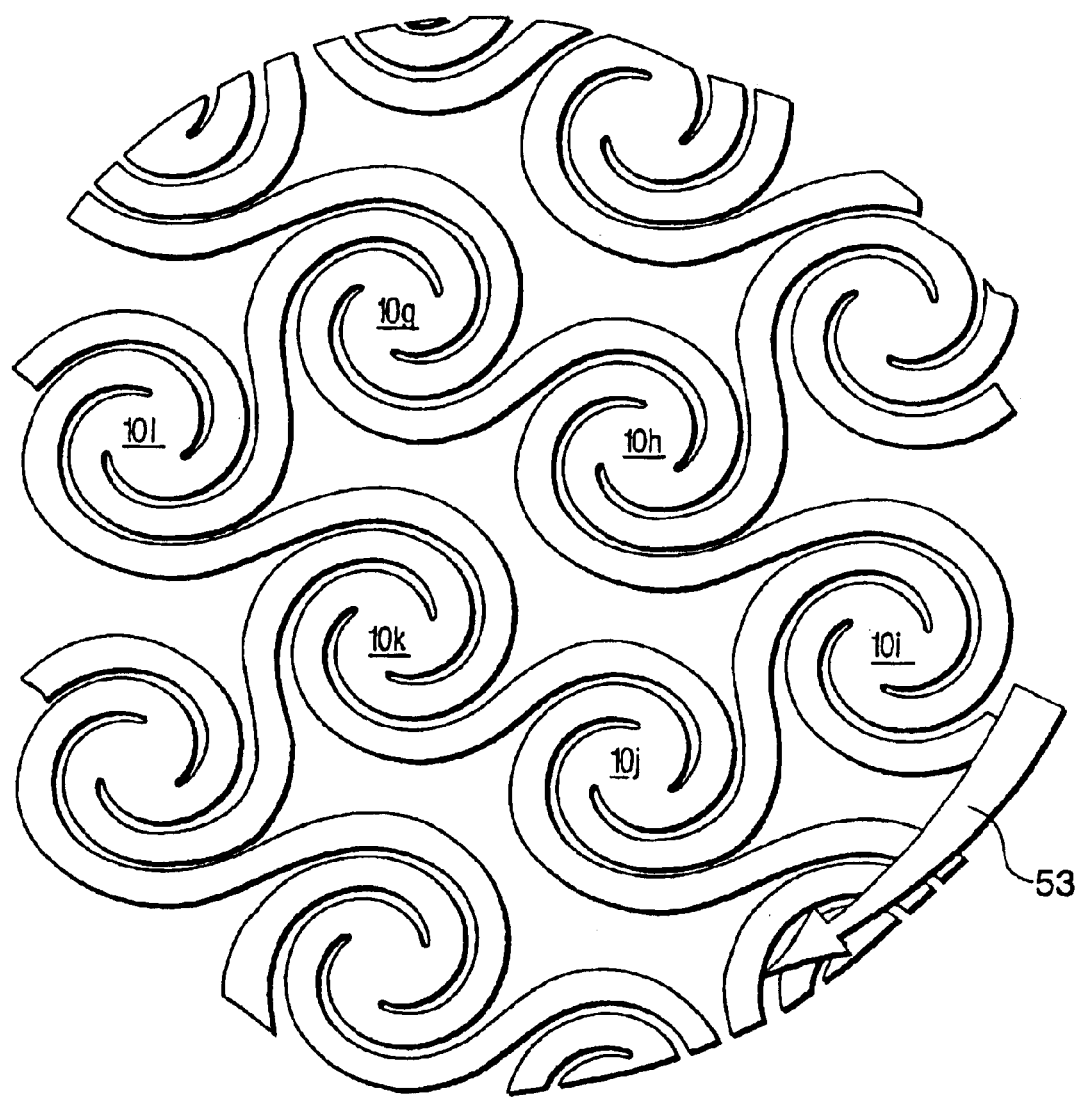
FIG. 14 is an enlarged illustration of a portion 12" of the embodiment of FIG. 12 illustrating the arrangement of a cluster of nodes.
Figure 14A:
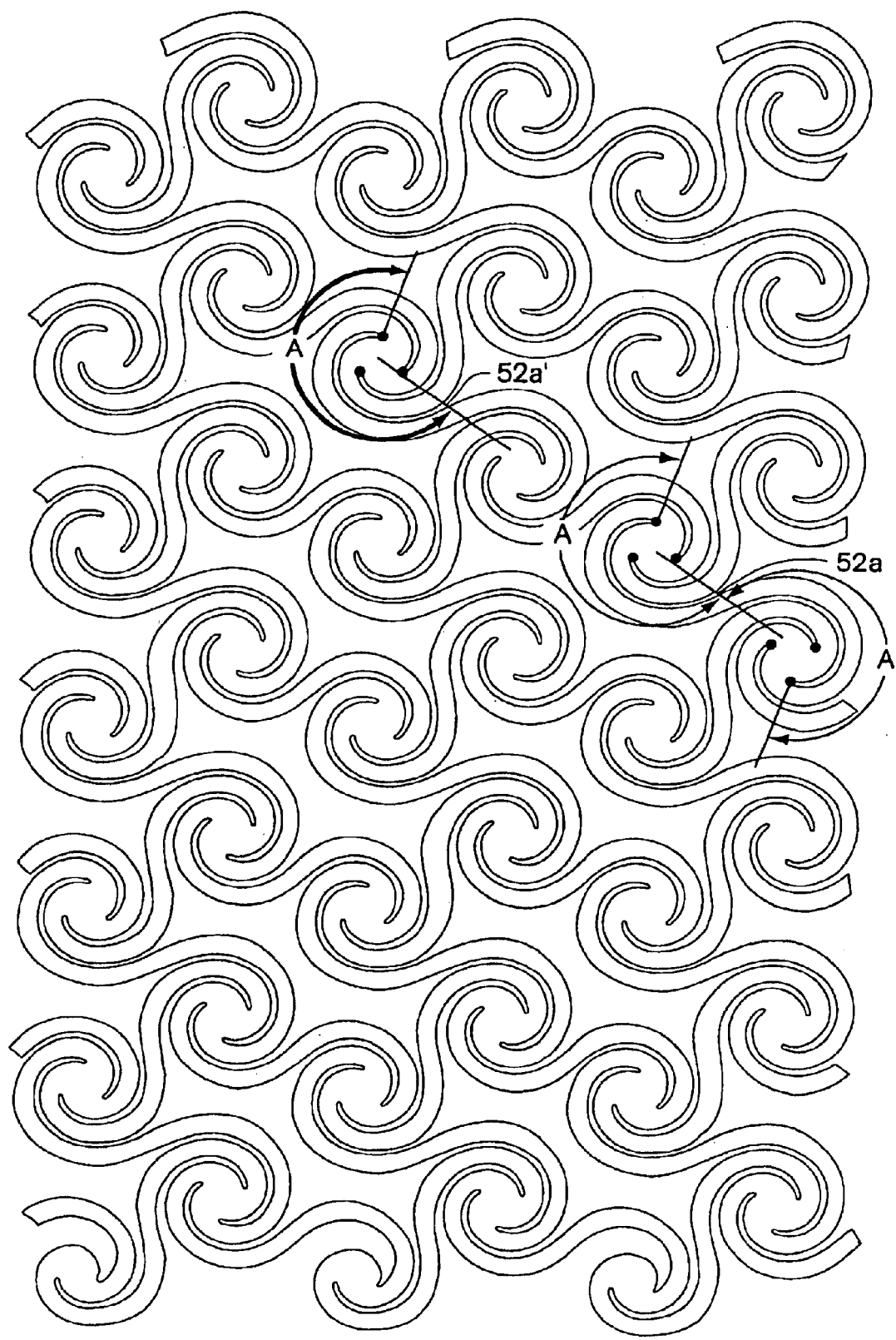
FIG. 14A is an illustration similar to FIG. 14, showing in more detail, a slight offset from a helical line of two sequential pairs of nodes.

The nodes 10 may be configured so that the arms 20 wrap closely about the hub of the node in order to maximize the extent to which the arms can unwind from their low profile to their expanded configuration. FIG. 4 illustrates, in further enlargement, the relationship between the nodes of an hexagonal cluster and of an adjacent hexagonal cluster, in which two of the nodes are common to both clusters. As shown in FIGS. 4 and 5, each node 10 may be considered to have three arms 20a, 20b and 20c, joined, respectively, at roots 22a, 22b, 22c, to the central hub 24 of the node. Each of the arms 20 extends from its root 22 and circumscribes its associated hub 24. Each of the arms 20a also circumscribes a portion of the next adjacent arm in the node. Thus, arm 20a circumscribes and lies closely adjacent a portion of arm 20c which, in turn, circumscribes and lies closely adjacent a portion of the arm 20b that, in turn, circumscribes and lies closely adjacent a portion of the arm 20a. The arms 20a, 20b and 20c may be considered as being arranged in a generally spiral pattern. A stent having nodes in which the arms define a larger arc between its root and its transition will tend to exhibit a greater expansions ratio from the compacted diameter to its maximum expanded diameter. FIG. 14A (described in further detail below) illustrates a stent configuration in which the nodes have arms that define an arc A extending between the root of an arm along the outer edge of the arm to the transition region 26 of that link. Also, as shown in FIG. 14A, the angle A extends over an arc of nearly 270°, with an angle of 254° being shown. Each of the arms 20a, 20b, 20c also may be considered as being joined to the outer region of an arm 20 of an adjacent node, the two arms being connected at a transition region 26. Each pair of connected arms 20 may be considered as a link 28 (FIG. 7) that extends from the root 22 of an arm 20 of one node to the root 22 of an arm 20 of an adjacent node, thus defining a connection between each pair of adjacent nodes 10. Each of the links 28 may be considered to define an S-shaped configuration in which the pair of arms 20 that defines a link 28 curve in opposite directions on either side of the transition region 26. A link 28 may be considered as extending along a direction that includes the roots 22 and transition region 26 of that link. Adjacent nodes 10 are connected to each other by one link 28.

In the hexagonal cluster configuration described above, the tubular stent may be considered as having a plurality of longitudinally spaced radial planes 30A, 30B (FIG. 4) that alternate lengthwise of the stent. The stent also may be considered as having a plurality of pairs of circumferentially adjacent nodes (10d, e and 10c, a), each pair of nodes being disposed in one or the other of the radial planes 30A, 30B. In the illustrative embodiment, the circumferentially adjacent nodes 10 are connected by a circumferentially oriented link 28 in which the hubs and, preferably, the roots 22 and transition region 26 of that link are disposed substantially along the radial plane 30A or 30B of the pair of nodes connected by that link 28 (FIGS. 4 and 5). When the stent is expanded, as by a balloon, the radially outward directed force of the balloon will translate to a circumferential force on the tubular stent that causes the circumferentially aligned pairs of nodes to separate, in a direction generally circumferential of the stent. That expansion tends to straighten the circumferentially oriented links. As an adjacent pair of circumferentially aligned nodes is urged apart, the circumferential link connecting those nodes will tend to become straightened while the hubs of the adjacent nodes are free to shift, as necessary, in order to accommodate the straightening of the circumferential link.

The stent embodiment described above also may be considered as defining pairs of longitudinally extending rows 32A, 32B that are circumferentially spaced about the stent. The arrangement of nodes with respect to the longitudinal rows 32A, 32B is one in which the nodes of each pair of adjacent nodes in an individual cluster lie along an alternate one of rows 32A, 32B. Consequently, adjacent nodes are not aligned along a longitudinal row but, instead, are aligned in a generally helical orientation or circumferential orientation, as indicated by the helical rows 34A, 34B and circumferential rows 30A, 30B.

Figure 15A:
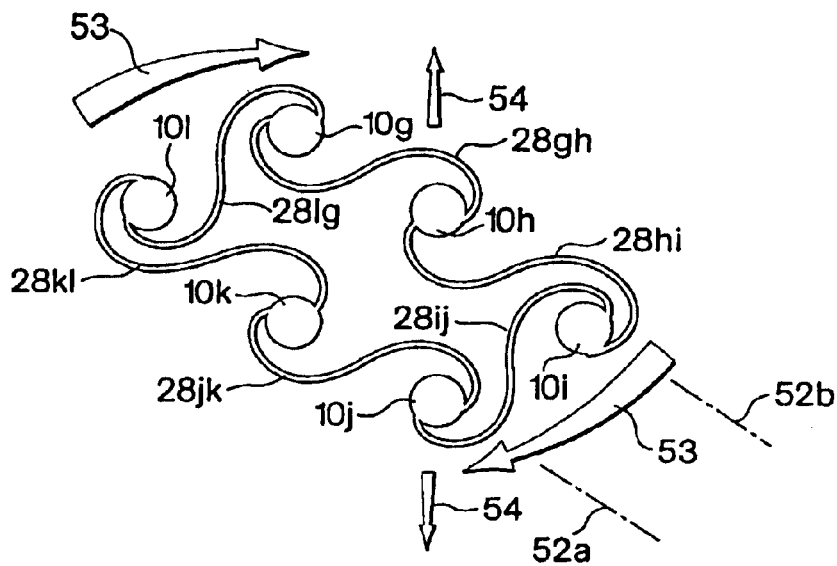
FIGS. 15A–15C are diagrammatic illustrations of the cluster shown in FIG. 14 showing the manner in which the nodes and interconnecting links shift about as the stent is forcibly expanded.
Figure 15B:
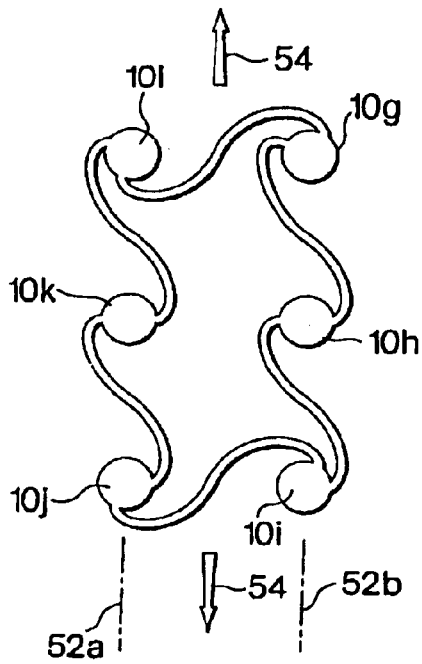
Figure 15C:
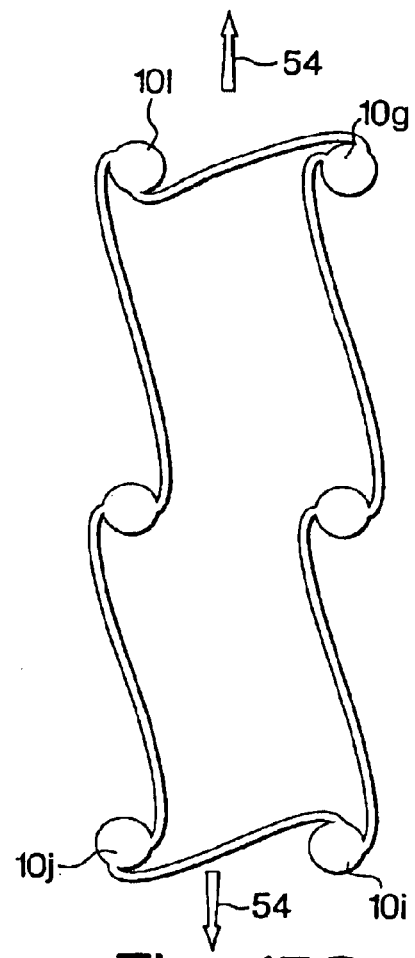

When the foregoing pattern is embodied in a balloon expandable stent, the circumferentially oriented links 28 will be the most deformed from their S-shaped configuration, because the principal direction of expansion is radial. The links 28 that extend in a generally helical direction (along the helical axes 34A, 34B) are free to expand differentially to be self-accommodating to the forces and strains imposed on the stent as it is expanded. Those links 28 that are not circumferentially oriented will expand to a lesser degree than circumferentially oriented links. This is illustrated diagrammatically in FIGS. 15A–15C in connection with another embodiment, described in further detail below. FIGS. 15A–15C which shows, diagrammatically, a portion of the stent during and after expansion, where the circumferentially oriented links have been expanded and straightened more than the non-circumferentially oriented links. The extent to which the stent is expanded will be determined as a function of the geometry of the stent, the expanded diameter of the relatively inelastic balloon of the delivery catheter and the anatomy of the body lumen into which the stent is to be placed.

The invention may be used with equal facility in short stents as well as in long stents, the length of the stent being selected to correspond to the anatomy into which the stent is to be placed. The high degree of flexibility achievable with stents made in accordance with the invention enables relatively long stents (e.g. of the order of 100 mm, as might be used in a bile duct) to be made and be deliverable, even where the path leading to the deployment site is tortuous. The wall thickness of the tube from which the stent is made preferable is of the order of 0.007 inches. The width of the links 28 preferably is less than the dimension of the wall thickness and may be of the order of about half of the wall thickness (e.g., about 0.0035 inches). By maintaining the width of the links 28 relatively narrow, the nodes can be made to be disposed closer to each other to facilitate formation of a relatively compact, dense array. After the stent pattern has been cut in the tube the stent then may be electropolished to put a slight radius on the edges of the stent members that remain after the laser cutting has been completed. In a stent having the hexagonal pattern shown in FIGS. 3 and 4, the stent may be cut from a tube having a diameter of the order of 0.080 inches that can be expanded to a diameter of about 7 mm, presenting an expansion ratio of approximately 3:1. Other embodiments, described below, can be configured with the nodes more closely packed (see, for example, the pattern shown in FIG. 12) in which a stent formed from a tube having a diameter of the order of 0.095 inches is expandable to a diameter of about 10 mm, providing an expansion ratio of about 5:1.

Also among the advantages of the present invention is the ability of the stent to maintain a high degree of flexibility both in its low profile configuration as well as after it has been expanded and deployed at the intended target site in the body lumen. The flexibility of the stent in its low profile configuration is important during the navigation of the delivery catheter to the deployment site, particularly when sharply curved, tortuous or other non-linear or irregular pathway to the deployment site is presented. When a balloon catheter is operated to expand the stent at the intended deployment site, the relatively inelastic balloon will assume its characteristic elongate, straight shape under the influence of the pressure of the inflation fluid. That, in turn, tends to straighten the portion of the vessel in which it is located. The flexibility of the stent, when expanded, is desirable in order that, after the delivery catheter has been removed, the stent can flex with the vessel as the vessel tends to return to its natural shape. A high degree of expanded stent flexibility thus will provide relatively low resistance to the vessel as it tends to return to its natural shape. This characterization of the invention is achieved while maintaining a high level of hoop strength for the stent.

The excellent longitudinal flexibility of the stent, particularly when in its low profile configuration, is considered to be the result of the use of the node construction described above in which the nodes also display an ability to flex or deform somewhat in a radial direction. The ability to flex in a radial direction (that is, in a direction perpendicular to the tubular wall and toward and away from the longitudinal axis of the stent), is the result of the spiral-like configuration of the arms about the hub of each node. The arms in each node can flex radially, thus enabling the hub to flex slightly, but sufficiently, toward or away from the stent longitudinal axis. The ability of the hub to flex radially is believed to result in a progressive and gradual flexure along the length of the stent with a reduced tendency to develop sharp kinks, and contributes to the high longitudinal flexibility of the invention.

Figure 8:
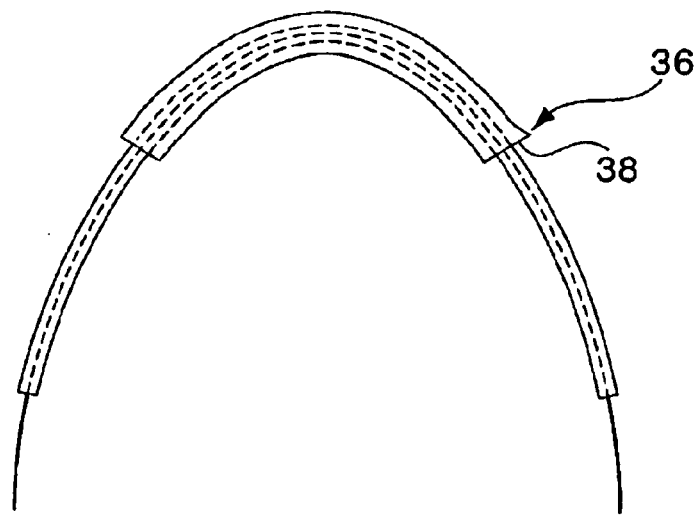
FIG. 8 is a diagrammatic illustration of a stent mounted on a catheter after having been advanced through a sharp bend and illustrating the manner in which the leading edge of the stent has become permanently deformed to a "fishmouth" configuration.

Also among the advantages of the invention is that it tends to avoid formation of a "fishmouth" condition at an end of a stent that is advanced, while mounted on the delivery catheter, through tortuous anatomy. As shown in FIG. 8, it is not uncommon for a stent, at its leading end 36, to develop an asymmetrical flare, somewhat like an open fishmouth, in which a portion of the leading end of the stent deforms to a flared shape and remains separated from the surface of the delivery catheter. The presence of such a flare 38 can present an obstacle to further advancement of the catheter and stent. It may cause damage to the interior surface of the lumen of the vessel and may become caught in a manner that may cause the stent to shift its longitudinal position on the delivery catheter before the stent has been advanced to the intended deployment site. Among the advantages of the present invention is that it displays reduced tendency for such flaring and, consequently, tends to avoid such difficulties.

Figure 9A:
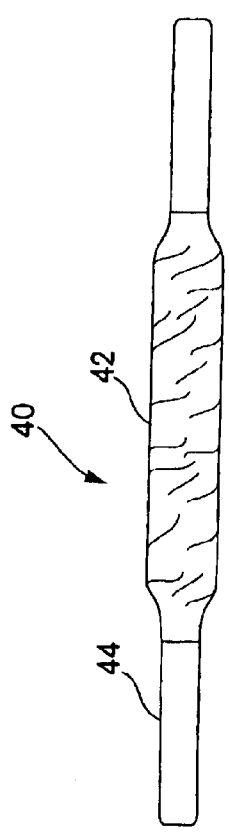
FIGS. 9A–9C illustrate an aspect of the invention in which a stent may be mounted onto a balloon catheter.
Figure 9B:
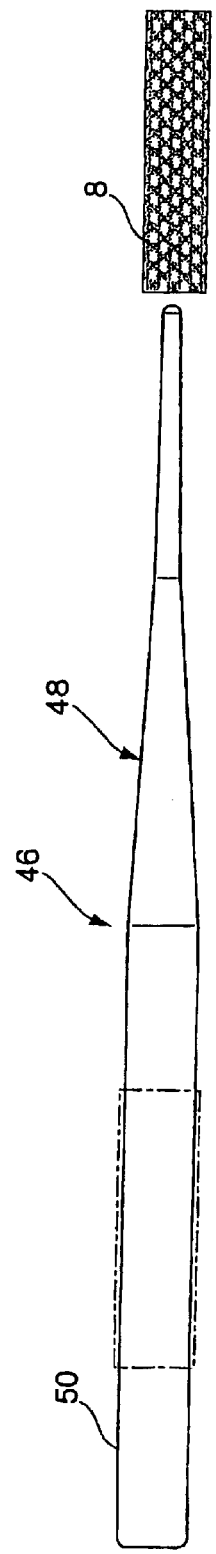
Figure 9C:
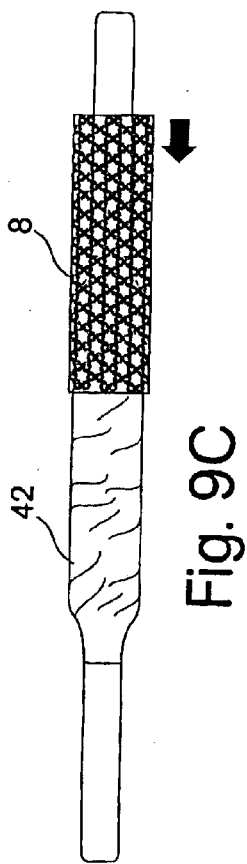

In order that a stent can achieve its maximum range of expansion, it is desirable to mount the stent on the delivery catheter in a profile that is as low as can be achieved with the particular stent configuration and geometry. To that end, the stent preferably is fabricated in its intended lowest profile configuration corresponding to what would normally be the diameter to which the stent is crimped onto the balloon of the delivery catheter. In the context of the stent described above, therefore, the stent is formed from a tube of metal with the nodes being cut out and located in as close proximity to each other as can be achieved for the particular stent pattern. When a stent, so formed, is to be mounted on a balloon catheter 40, the balloon 42 will have been wrapped tightly about itself and the catheter shaft 44 (FIG. 9A). In order to mount the stent on the balloon, the stent is preliminarily expanded slightly to "size" the stent to the balloon. Such stent sizing may be achieved by inflating a small diameter balloon within the stent or by passing a mandrel 46 through the stent in which the mandrel has a tapered leading end 48 and a slightly enlarged trailing end 50 (FIG. 9B). The stent is expanded just slightly, enough to slip it onto the balloon of the catheter (FIG. 9C). Because the stent was expanded from its low profile configuration in which it was fabricated, the stent then can be crimped down tightly about the balloon, causing the stent to be secured to the balloon while also compacting the stent back toward or, if permitted by the laser-cut dimensions, slightly beyond its originally formed profile. By initially fabricating the stent in its low profile diameter and then expanding it slightly to place it on the balloon, it is assured that when crimped back toward its fabricated diameter, the nodes will not collide or otherwise interfere with each other.

Figure 10:
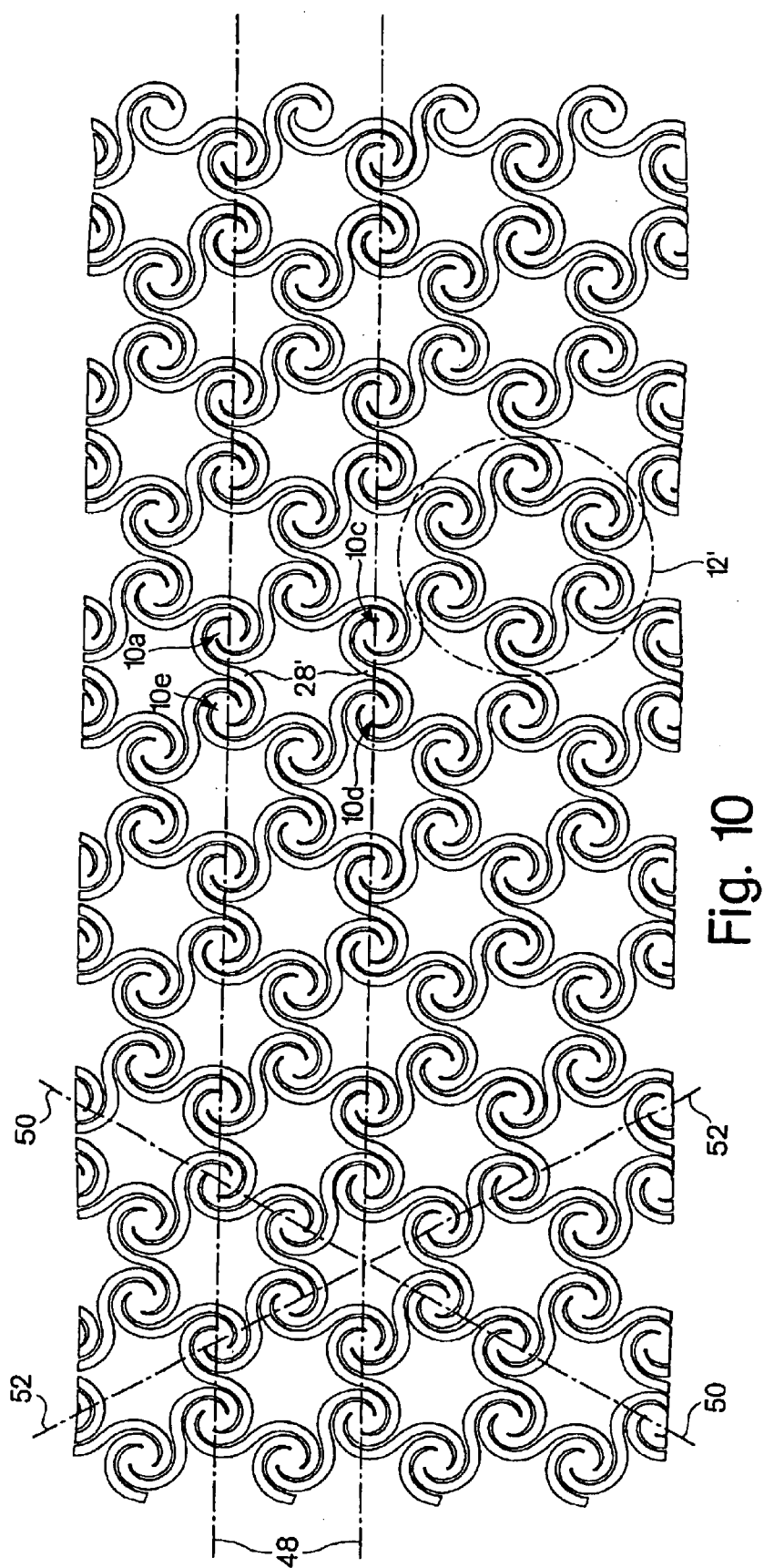
FIG. 10 is a flat plane illustration of a stent pattern having hexagonal clusters of nodes in which the orientation of the clusters has been modified.
Figure 11:
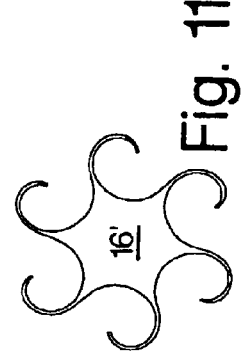
FIG. 11 is a diagram of the repeating cell pattern defined by a single hexagonal cluster of nodes as show in FIG. 10.

FIG. 10 illustrates a modified embodiment of the invention in which the hexagonal clusters 12 are oriented so that adjacent pairs of nodes (e.g., 10a, 10e and 10c, 10d) are aligned substantially parallel to the longitudinal axis of the stent such that the link 28' connecting the nodes in each of those pairs extends longitudinally of the stent. In this embodiment, the transition region 26 of the connecting links 28' and their hubs 22 lie along lines 48 that parallel the longitudinal axis of the stent. Those adjacent pairs of nodes that are not longitudinally aligned are disposed along rows 50, 52 that are generally helically disposed about the stent. In this embodiment, none of the adjacent pairs of nodes extends in a purely circumferential direction. FIG. 10 illustrates the configuration of a characteristic cell 16 of the stent pattern of FIG. 10.

Figure 12:
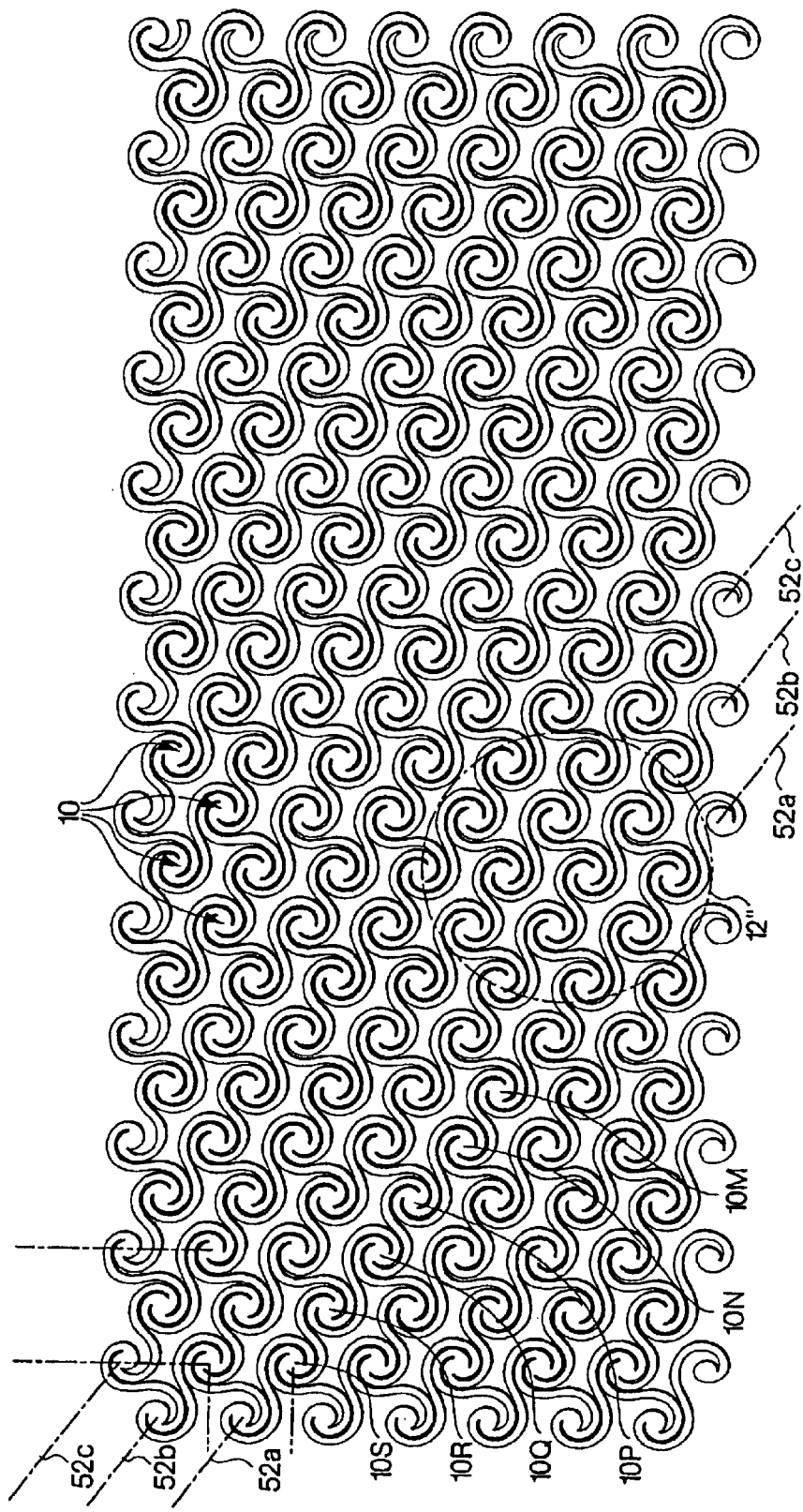
FIG. 12 is a flat plane illustration of the pattern of another embodiment of a stent in accordance with the invention in which the nodes are packed more closely together than with the hexagonal cluster.
Figure 13:
FIG. 13 is a diagram of the repeating cell pattern of the stent having the pattern shown in FIG. 12.

FIG. 12 illustrates a modified embodiment of the invention in which the nodes are more closely compacted than with the hexagonal cluster configurations described above. In this embodiment the nodes 10 may be considered as being generally aligned along helically extending rows 52A, 52B, 52C, with adjacent nodes along each helical row being serially connected to each other by an individual link 28''. Thus for each node 10 two of the three arms 20 form links 28'' to adjacent nodes along the same row. Each node also includes an arm 20' that forms a portion of a third link 28''' that is connected to a node in an adjacent helically oriented row. The third links of the nodes alternate from one node to the next along a given helical row. Thus, considering helical row 52B as a first row, one node in that row will include a link 28''' that connects to a node in a second adjacent helical row 52A while the next succeeding node in the first row has a third link that connects to a node on the adjacent helical row 52C on the other side. It should be noted that, it may be desirable in this embodiment, in order to avoid interference between the nodes, to shift successive pairs of nodes that lie along a helical row to a position that is slightly offset from a precise helical line. Thus, although nodes 10m, 10n, 10p, 10q, 10r, 10s are all disposed generally along the helical row 52a, it may be necessary for adjacent pairs (e.g., 10p, 10q) in the helical rows to be shifted very slightly laterally with respect to the immediately preceding pair (10m, 10n). Thus, node pair 10m, 10n may be considered as defining a line that lies along the helical row 52a while the node pair 10p, 10q may define a line that parallels helical line 52a but is displaced slightly (a few thousandths of an inch) to one side of line 52a. The slight displacement is illustrated in FIG. 14A from which it may be seen that helical line 52a' is displaced slightly to one side of line 52a. For ease of description, the series of nodes 10m–10s nonetheless may be considered as lying generally along a helical row. It should be noted that those nodes that lie along a row that extends longitudinally of the stent or along the plane that extends transversely of the tubular stent can be aligned without displacement such that all of the orthoginally related nodes may be considered as being more precisely in alignment along the longitudinal direction and along radial planes than the less precisely aligned nodes that extend along the helical rows.

FIGS. 14 and 15A–C illustrate in diagrammatic fashion, the manner in which a stent patterned as shown in FIG. 12 may expand under the influence of an expanding balloon. The cluster is shown, in enlarged detail, and includes six nodes 10g, 10h, 10i, 10j, 10k, 10l. As the cluster is subjected to the forces of radial expansion of the balloon, indicated by arrows 54, the cluster tends to rotate in a clockwise direction as illustrated by arrows 53 in FIGS. 14 and 15A–15C. During such cluster rotation the links 28 in the cluster will tend to expand, although at a relatively slow rate, until the cluster has rotated to a more circumferential orientation (FIG. 15B). As the cluster approaches a more circumferential orientation, the rate at which the links begin to expand increases. Thereafter, continued radial expansion of the balloon causes the circumferentially oriented links (28gh, 28hi, 28jk, 28kl) to expand toward their full expandable lengths (FIG. 15C).

As shown in FIGS. 15A–15C, as the cluster rotates clockwise during the initial portion of the balloon expansion, the links 28lg and 28ij that connect the endmost pairs (10g, 10l and 10l, 10j) of the cluster will become reoriented to extend generally along lines that are more parallel to the longitudinal axis of the stent than when the stent is in its low profile configuration. As those links rotate into a more longitudinal orientation, they become positioned to resist longitudinal compression of the stent. Consequently, the reorientation of those links results in an increase in the-resistance to shortening of the stent as the stent is expanded radially.

The ends of the stent may be finished, for example, as indicated in FIG. 4, in which an arm of each of the nodes in the endmost radial plane 30E is connected to another arm of another node in that plane. One such arrangement is illustrated in FIG. 4 from which it can be seen that links x, y, each of which extends from a node in the endmost radial plane 30A is connected, as by a connecting link z. The connecting link and the ends of the links x and y are joined at a junction that may be considered as defining a partial, two-armed node in which the arms have portions that parallel each other in a generally spiral configuration. It should be understood, however, that other arrangements for connecting the nodes in the endmost radial planes of the stent may be employed.

Figure 16:
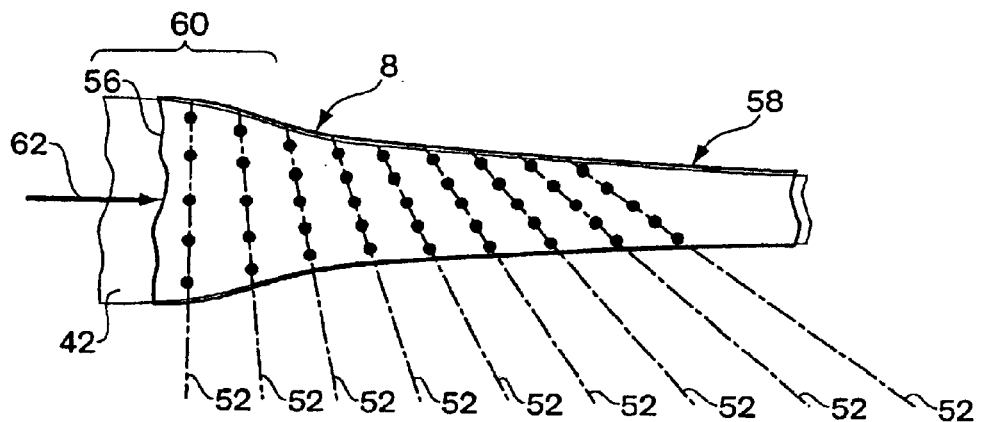
FIG. 16 is a diagrammatic illustration of a stent during expansion on a balloon showing the manner in which the end of the stent may tend to expand before the midportion of the stent.

In another aspect of the invention, the ends of the stent may be configured to present a greater resistance to radial expansion than the portions of the stent intermediate the ends. FIG. 16 illustrates, diagrammatically, a phenomenon associated with balloon expandable stents in which the ends 56 of the stent 8 tend to begin to expand before the mid-portion 58 of the stent. As a result, the ends of the balloon, in the early stages of expansion, may flare so that the balloon and stent assume a "dog bone" configuration in which the end regions 60 of the balloon 42 are expanded to a greater diameter than the mid-portion of the balloon. The expansion of the ends before the middle of the stent tends to develop a compressive end loading, indicated at arrow 62, being placed on the end regions of the stent. The compressive loading on the end regions may tend to shorten the end regions until the mid-portion of the balloon has expanded, at which time continued balloon expansion will be more uniform along its length. It is desirable to minimize the extent of stent shortening during expansion because such shortening can result in the stent being deployed in a position shifted from that which was intended. Additionally, shortening of the stent during expansion may result in the deployed stent having insufficient length to support the entire length of lumen intended.

Figure 17:
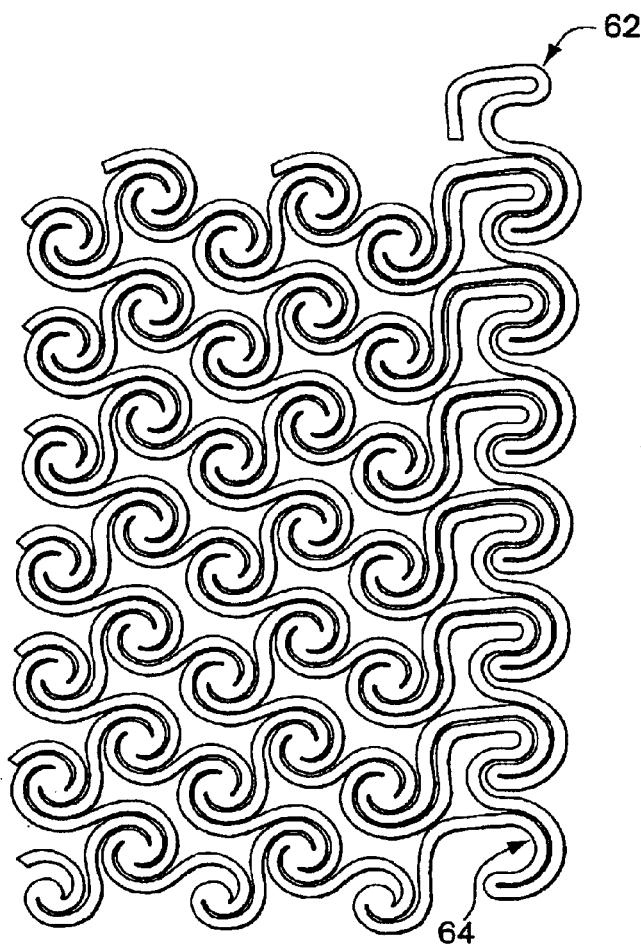
FIG. 17 is an illustration of an end portion of a stent, in the flat, showing the configuration by which the end may be interlocked to provide increased resistance to the expansion of the end of the stent.
Figure 18:
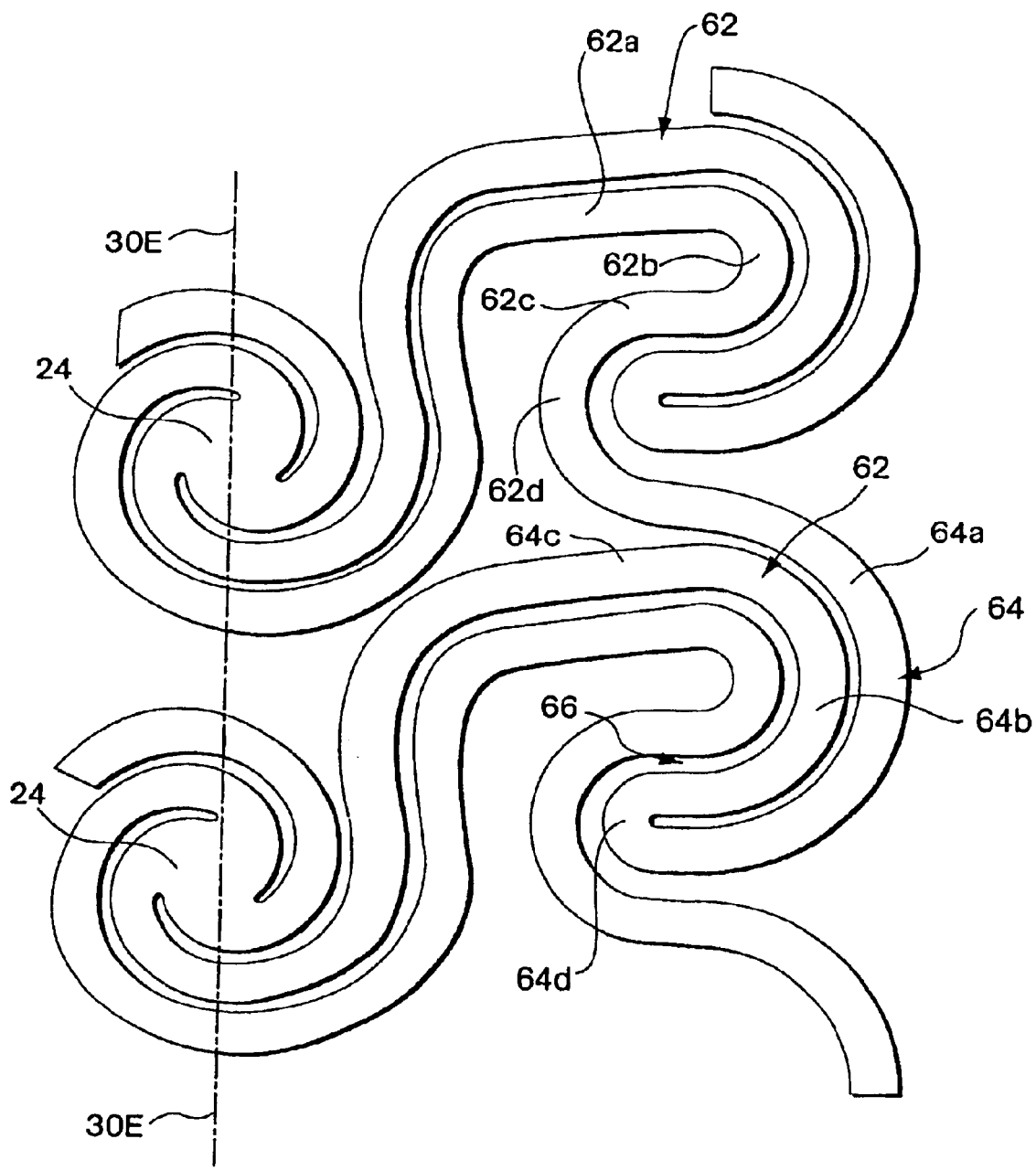
FIG. 18 is an enlarged illustration of the details of the interlocking arrangement of FIG. 17.

FIGS. 17 and 18 illustrate another embodiment of an arrangement for increasing the resistance to expansion at the ends of the stent, discussed above, sufficiently to reduce, and possibly to eliminate, the longitudinal shortening at the end regions of the stent during the early part of the balloon expansion. The arrangement includes a series of interlocked elements at the end of the stent that resist expansion, at least during the early portion of balloon expansion. The interlocked components are formed from extensions of arms of nodes in the endmost radial plane 30E and may be considered to include an L-shaped member 62 and an L-shaped socket 64 receptive to the member 62. The member 62 and the socket 64 are formed by extensions of arms of adjacent nodes at the end of the stent. The arm of one node is extended to define a series of serpentine legs 62a, 62b, 62c, 62d that define the L-shaped member. The extension continues to include a pair of sequential legs 64a, 64b that parallel each other and are joined at a hairpin bend 64d. Legs 64a and 64b thus define a double thickness socket that captures an L-shaped member. The portion of the L-shaped member, including legs 62c and 62d define a second socket 66 that receives the hairpin bend 64d of the socket legs 64a, 64b. It should be understood that in the illustrations, the space between the legs that make up the L-shaped member 62 and L-shaped socket 64 are spaced apart sufficiently for clarity of illustration. As discussed above, the space between adjacent paralleling components (such as 64a, 64b) of the stent may be as small as the width of the laser beam by which the pattern is cut, for example, about 0.002 inch. Thus, the distal ends of the stent preferably are provided with a configuration that differs from the spiral configuration of the nodes and which includes interlocking members that will present resistance to stent expansion as the balloon is inflated. The spaces between the interlocking components, however, should be sufficient so that at a desired point in the expansion of the balloon, the interlocking components will have deformed sufficiently to release, thereby enabling the end of the stent to continue expansion together with the midportions of the stent.

From the foregoing, it may be appreciated that the invention provides a stent construction that may be used to achieve a high degree of stent flexibility both when in a low profile configuration as well as when in an expanded configuration. The invention enables a stent to be configured in a low profile while being expandable through a substantial range of larger diameters. The stent may be configured in a manner that lessens the degree of stent shortening as the stent is deployed and provides additional benefits discussed above.

It should be understood however, that the foregoing description of the invention is intended merely to be illustrative thereof and that other modifications, embodiments and equivalents may be apparent to those who are skilled in the art without departing from its spirit.

Having thus described the invention what I desire to claim and secure by letters patent is:

1. A radially expandable intraluminal stent in the form of a generally tubular wall having open regions that define wall structure comprising: a plurality of nodes, each node having a central hub and only three arms extending from the hub, each arm being curved and circumscribing the hub and a segment of an adjacent arm of that node; each arm being connected, at a transition region, only to a single arm of an adjacent node, the connected arms of adjacent nodes defining an S-shaped link between those nodes.

2. A stent as defined in claim 1 wherein the portion of each arm that circumscribes the segment of the adjacent arm of that node lying closely adjacent the segment.

3. A stent as defined in claim 1 wherein nodes are arranged in hexagonal clusters.

4. A stent as defined in claim 3 wherein the hexagonal clusters are oriented so that none of adjacent pairs of nodes in the clusters is aligned in a direction that parallels the longitudinal axis of the stent.

5. A stent as defined in claim 3 wherein the hexagonal clusters are oriented so that none of adjacent pairs of nodes in the clusters is aligned in a circumferential direction of the stent.

6. A stent as defined in claim 1 wherein the arms of each of the nodes are arranged generally to define a spiral.

7. A stent as defined in claim 6 wherein a gap between adjacent arms of the spiral is of substantally constant width up to the transition region.

8. A stent as defined in claim 1 wherein each of the arms of a node is connected at a root to the hub of the node and wherein the roots are equiangularly spaced about the hub.

9. A stent as defined in claim 1 wherein each arm of each node is connected to a different one of the adjacent nodes.

10. A stent as defined in claim 1 further comprising:
the nodes being arranged so that a plurality of adjacent connected pairs of nodes lie along radially extending planes, the planes being spaced along the length of the stent.

11. A stent as defined in claim 10 wherein links between the nodes of said connected pairs thereof lie along the radial planes and extend in a circumferential direction of the stent.

12. A stent as defined in claim 11 further comprising additional connected pairs of adjacent nodes extending along a row that extends generally helically along the stent.

13. A stent as defined in claim 1 further comprising:
the nodes being arranged so that a plurality of adjacent pairs of nodes lie along a row extending longitudinally of the stent.

14. A stent as defined in claim 13 wherein the nodes are arranged to define a plurality of said longitudinally extending rows.

15. A stent as defined in claim 1 wherein the transition region is disposed at the mid portion of the link.

16. A stent as defined in claim 1 formed from a metal having sufficient ductility to plastically deform in response to application of a radially outward expansion force applied to the stent.

17. A stent as defined in claim 1 formed from a material having sufficient inherent resilience to cause the stent to itself expand from a low profile diameter to an expanded diameter.

18. A stent as defined in claim 1 formed from a metal having shape memory characteristics adapted to enable the stent to expand in response to a thermal event.

19. A stent as defined in claim 1 having low profile and expanded diameters and being dimensioned to enable the stent to be delivered into and deployed within a human biliary duct.

20. A stent as defined in claim 1 having low profile and expanded diameters to enable the stent to be delivered into and deployed within a blood vessel.

21. A stent as defined in claim 1 having low profile and expanded diameters and being dimensioned to enable the stent to be delivered into and deployed within a urological passage.

22. A stent as defined in claim 1 further comprising clusters, each cluster being formed from six nodes.

23. A stent as defined in claim 1 further comprising the nodes being arranged in clusters of six, two arms of each node are connected to the nodes of a same cluster and one arm of each of the nodes in that cluster is connected to a node of another cluster.

24. A stent as defined in claim 23 wherein each of the nodes in the stent is shared by three adjacent clusters.

25. A radially expandable intraluminal stent in the form of a generally tubular wall having open regions that define wall structure comprising: a plurality of nodes, each node having a central hub and only three arms extending from the hub, each arm having a root and being curved and circumscribing the hub and a segment of an adjacent arm of that node and lying closely adjacent the segment; each arm being connected, at a transition region only to a single arm of an adjacent node, the connected arms of the adjacent nodes defining a link between those nodes, the link extending from the root of one of the connected arms to the root of the other, wherein the link curves in one direction from one root to the transition region and in an opposite direction from the transition region to the other root.

26. In a radially expandable tubular intraluminal stent defined by and having a plurality of interconnected members deformable to a larger diameter tubular configuration, the improvement comprising a plurality of nodes, each defined by a central hub and only three arms, each of the arms in each of the nodes being curved and having a portion that circumscribes the hub and a segment of an adjacent arm of that node and lies closely adjacent the segment, the stent being defined substantially entirely by said nodes, each arm being curved and being connected at a transition region to a single arm of an adjacent node, the connected arms of adjacent nodes defining an S-shaped link between those nodes.

27. A stent as defined in claim 26 wherein nodes are arranged in general alignment along a plurality of helically extending rows, two of the arms of each node being connected serially to adjacent nodes along its associated helical row, the third arm of the node being connected to a node that lies along an adjacent helical row.

28. A stent as defined in claim 27 wherein the third arm of succeeding nodes lying along a helical row are connected to nodes in alternately adjacent helical rows.

29. A stent as defined in claim 26 further in which the arms define a generally spiral configuration.

30. A stent as defined in claim 29 wherein the nodes are arranged in clusters of six nodes each.

31. A stent as defined in claim 29 wherein the nodes are arranged along a plurality of helical rows, the nodes in each row being serially connected to each other by a link, each of the nodes in each helical row also being connected, by a link, to a node in each adjacent helical row.

32. A stent as defined in claim 26 further comprising:
a gap defined between each arm and a segment of an adjacent arm, the gap being of substantially constant width.

33. A radially expandable intraluminal stent in the form of a generally tubular wall having cut out regions that define wall structure comprising: a plurality of nodes, each node being connected only to three adjacent nodes, each by an individual generally S-shaped link, some of which are circumferentially oriented; the links and nodes being arranged so that when the stent is expanded from its initial diameter to an expanded diameter, circumferentially oriented links will elongate to a greater degree than links oriented in a less circumferential direction.

34. In a radially expandable tubular stent having a wall defined by and having a plurality of interconnected links deformable from a low profile diameter to an expanded diameter, the improvement comprising a plurality of nodes, each node having a central hub and only three arms extending from and circumscribing the hub and a segment of an adjacent arm of that node, the arms being of sufficient length to flex to permit the central hub to be displaced transversely with respect to those regions of the stent wall that surround the transversely displaced hub, each of the arms being connected to an arm of an adjacent node to define an S-shaped link.

35. A radially expandable intraluminal stent in the form of a generally tubular wall having open regions that define wall structure comprising: a plurality of nodes, each node having a central hub and only three arms extending from the hub, each arm circumscribing the hub and a segment of an adjacent arm of that node and lying closely adjacent the segment; each arm being connected, at a transition region, only to one arm of an adjacent node, the connected arms of the adjacent nodes defining an S-shaped link between those nodes.

36. A radially expandable intraluminal stent in the form of a generally tubular wall having open regions that define wall structure comprising: a plurality of nodes, each node having a central hub and only three arms extending from the hub, each arm circumscribing the hub and a segment of an adjacent arm of that node; each arm being connected, at a transition region, to an arm of an adjacent node, the connected arms of the adjacent nodes defining a substantially continuously curving S-shaped link between those nodes.

37. A radially expandable intraluminal stent in the form of a generally tubular wall having open regions that define wall structure comprising: a plurality of nodes, each node having a central hub and only three arms extending from the hub, each arm circumscribing the hub and a segment of an adjacent arm of that node and defining a gap between the adjacent arm; each arm being connected, at a transition region, to an arm of an adjacent node, the connected arms of the adjacent nodes defining an S-shaped Ink between those nodes; the gap being of substantially constant width up to the transition region.

* * * * *